US009398913B2

United States Patent
Tegels et al.

(10) Patent No.: US 9,398,913 B2
(45) Date of Patent: Jul. 26, 2016

(54) SEALANT STORAGE, PREPARATION, AND DELIVERY SYSTEMS AND RELATED METHODS

(71) Applicant: St. Jude Medical Puerto Rico LLC, Caguas, PR (US)

(72) Inventors: Zachary J. Tegels, Minneapolis, MN (US); Russell D. Terwey, St. Michael, MN (US); Troy T. White, Maple Grove, MN (US); Timothy M. McGlinch, St. Paul, MN (US); Bernhard Kaeferlein, Champlin, MN (US); Edward E. Parsonage, St. Paul, MN (US); Martha Escobar, Jordan, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 260 days.

(21) Appl. No.: 13/773,206

(22) Filed: Feb. 21, 2013

(65) Prior Publication Data
US 2014/0058442 A1   Feb. 27, 2014

Related U.S. Application Data

(60) Provisional application No. 61/692,859, filed on Aug. 24, 2012.

(51) Int. Cl.
*A61B 17/08* (2006.01)
*A61B 17/00* (2006.01)
(Continued)

(52) U.S. Cl.
CPC .............. *A61B 17/08* (2013.01); *A61B 17/0057* (2013.01); *A61B 17/00491* (2013.01);
(Continued)

(58) Field of Classification Search
CPC ............. A61B 17/08; A61B 17/00491; A61B 17/0057; A61B 2017/00495; A61B 2017/0065; A61M 5/19; A61M 5/2448; A61J 1/2096

USPC ............ 604/15, 48, 93.01, 81, 82, 83, 84, 85, 604/92, 153, 173, 181, 182, 187, 191, 252, 604/403, 500, 518, 502; 606/181, 213, 214; 141/18–29, 100–107; 251/9; 222/23
See application file for complete search history.

(56) References Cited

U.S. PATENT DOCUMENTS 3,236,418 A * 2/1966 Dalle .................. B65D 83/682
                                                    222/131
3,563,373 A * 2/1971 Paulson ................ A61J 1/2093
                                                    206/229
(Continued)

FOREIGN PATENT DOCUMENTS

EP          2384703 A1   11/2011
WO     2010091527 A1    8/2010

OTHER PUBLICATIONS

PCT International Search Report and Written Opinion for PCT International Application No. PCT/US2013/027067, mailed Jun. 26, 2013.
(Continued)

*Primary Examiner* — Katherine M Shi
*Assistant Examiner* — Mohamed Gabr
(74) *Attorney, Agent, or Firm* — Holland & Hart

(57) ABSTRACT

A bioadhesive sealant storage and preparation system may comprise a plurality of containers and an adapter. The plurality of containers may comprise a first container having a first bioadhesive sealant component therein, and a second container having a second bioadhesive sealant component therein. The adapter may comprise a manifold comprising a plurality of channels formed therein, an inlet region sized and configured to receive the plurality of containers and facilitate fluid communication between each container of the plurality of containers and a respective channel of the plurality of channels, and an outlet region sized and configured to receive a syringe and provide fluid communication between the syringe and the plurality of channels.

16 Claims, 8 Drawing Sheets

(51) Int. Cl.
*A61M 5/19* (2006.01)
*A61M 5/24* (2006.01)

(52) U.S. Cl.
CPC ............... *A61M5/19* (2013.01); *A61M 5/2448* (2013.01); *A61B 2017/0065* (2013.01); *A61B 2017/00495* (2013.01)

(56) References Cited

U.S. PATENT DOCUMENTS

| | | | | |
|---|---|---|---|---|
| 4,121,739 | A * | 10/1978 | Devaney | B05C 17/00553 222/137 |
| 4,180,070 | A * | 12/1979 | Genese | A61J 1/2089 604/414 |
| 4,328,802 | A * | 5/1982 | Curley | A61J 1/2096 604/88 |
| 4,458,733 | A * | 7/1984 | Lyons | A61J 1/2089 141/1 |
| 4,619,651 | A * | 10/1986 | Kopfer | A61J 1/2096 604/414 |
| 4,631,055 | A * | 12/1986 | Redl | A61B 17/00491 222/135 |
| 4,676,256 | A * | 6/1987 | Golden | A61B 5/1427 600/575 |
| 4,759,756 | A * | 7/1988 | Forman | A61J 1/2089 604/413 |
| 4,874,368 | A * | 10/1989 | Miller | A61B 17/00491 222/137 |
| 4,902,281 | A * | 2/1990 | Avoy | A61B 17/00491 222/137 |
| 5,147,323 | A * | 9/1992 | Haber | A61M 5/19 604/191 |
| 5,171,220 | A * | 12/1992 | Morimoto | A61J 1/2089 604/220 |
| 5,271,527 | A * | 12/1993 | Haber | A61M 5/19 222/137 |
| 5,329,976 | A * | 7/1994 | Haber | A61J 1/2089 141/18 |
| 5,360,410 | A * | 11/1994 | Wacks | A61M 5/20 604/110 |
| 5,423,752 | A * | 6/1995 | Haber | A61M 5/19 222/137 |
| 5,478,323 | A * | 12/1995 | Westwood | A61M 5/19 604/191 |
| 5,814,022 | A * | 9/1998 | Antanavich | A61B 17/00491 604/181 |
| 5,925,029 | A * | 7/1999 | Jansen | A61J 1/2096 604/403 |
| 6,099,504 | A * | 8/2000 | Gross | A61M 5/2046 604/140 |
| 6,113,571 | A * | 9/2000 | Zinger | A61B 17/00491 604/191 |
| 6,390,815 | B1 * | 5/2002 | Pond | A61C 1/0061 433/100 |
| 6,471,670 | B1 * | 10/2002 | Enrenfels | A61B 17/00491 604/191 |
| 6,508,791 | B1 * | 1/2003 | Guerrero | A61M 5/1408 604/183 |
| 6,557,651 | B1 * | 5/2003 | Norby | F16L 15/003 175/52 |
| 6,565,539 | B1 * | 5/2003 | Zinger | A61B 17/00491 604/191 |
| 6,610,033 | B1 * | 8/2003 | Melanson | A61B 17/00491 604/181 |
| 6,620,138 | B1 * | 9/2003 | Marrgi | A61M 5/1408 604/110 |
| 6,719,719 | B2 * | 4/2004 | Carmel | A61J 1/2089 604/191 |
| 7,037,289 | B2 * | 5/2006 | Dodge | A61B 17/00491 604/191 |
| 7,077,339 | B2 * | 7/2006 | Leach | A61B 17/00491 222/137 |
| 7,182,107 | B2 * | 2/2007 | Sommer | A61B 17/00491 141/100 |
| 7,608,055 | B2 * | 10/2009 | Griffiths | A61M 5/2033 604/191 |
| 7,611,494 | B2 * | 11/2009 | Campbell | A61B 17/00491 604/191 |
| 7,635,343 | B2 * | 12/2009 | McIntosh | A61B 17/00491 604/82 |
| 7,785,312 | B2 * | 8/2010 | Thorne, Jr. | A61J 1/2096 604/500 |
| 7,819,342 | B2 * | 10/2010 | Spallek | A61M 15/0065 222/137 |
| 8,333,787 | B2 | 12/2012 | Pipenhagen et al. | |
| 8,506,592 | B2 | 8/2013 | Killion et al. | |
| 8,821,436 | B2 * | 9/2014 | Mosler | A61J 1/2089 604/411 |
| 9,131,930 | B2 * | 9/2015 | Greter | A61B 17/00491 |
| 2001/0016709 | A1 * | 8/2001 | Tovey | A61B 17/00491 604/153 |
| 2003/0023203 | A1 * | 1/2003 | Lavi | A61J 1/2089 604/82 |
| 2003/0187408 | A1 * | 10/2003 | Marx | A61B 17/00491 604/236 |
| 2003/0233067 | A1 * | 12/2003 | McIntosh | A61B 17/00491 604/82 |
| 2004/0199139 | A1 * | 10/2004 | Fowles | A61J 1/1406 604/414 |
| 2004/0267308 | A1 * | 12/2004 | Bagaoisan | A61B 17/0057 606/213 |
| 2005/0027240 | A1 * | 2/2005 | Fehr | A61C 5/064 604/82 |
| 2005/0175665 | A1 * | 8/2005 | Hunter | A61K 45/06 424/423 |
| 2005/0192546 | A1 * | 9/2005 | Griego | A61M 25/0026 604/264 |
| 2006/0079846 | A1 * | 4/2006 | Williams | A61M 5/002 604/191 |
| 2006/0280690 | A1 * | 12/2006 | Wright | A61B 17/0008 424/45 |
| 2007/0012724 | A1 * | 1/2007 | Feinberg | A61B 17/00491 222/137 |
| 2007/0073267 | A1 * | 3/2007 | Muller | A61M 5/1408 604/506 |
| 2007/0088268 | A1 * | 4/2007 | Edwards | A61M 5/19 604/136 |
| 2007/0197954 | A1 * | 8/2007 | Keenan | A61B 8/0833 604/20 |
| 2007/0231366 | A1 * | 10/2007 | Sawhney | A61L 24/0031 424/426 |
| 2007/0286891 | A1 * | 12/2007 | Kettlewell | A61L 15/58 424/443 |
| 2008/0045925 | A1 * | 2/2008 | Stepovich | A61M 5/14566 604/518 |
| 2008/0060970 | A1 * | 3/2008 | Wheeler | A61B 17/00491 206/570 |
| 2008/0103564 | A1 * | 5/2008 | Burkinshaw | A61B 17/00491 607/96 |
| 2008/0114304 | A1 * | 5/2008 | Nalesso | A61M 5/19 604/191 |
| 2008/0161757 | A1 * | 7/2008 | Nayak | A61M 5/19 604/82 |
| 2008/0167621 | A1 * | 7/2008 | Wagner | A61M 5/19 604/191 |
| 2008/0215088 | A1 * | 9/2008 | Hnojewyj | A61B 17/0057 606/214 |
| 2008/0306436 | A1 * | 12/2008 | Edwards | A61M 5/19 604/67 |
| 2009/0062741 | A1 * | 3/2009 | Smith | A61M 5/19 604/191 |
| 2009/0099547 | A1 * | 4/2009 | Radmer | A61J 1/2089 604/519 |
| 2009/0131864 | A1 * | 5/2009 | Pickhard | A61M 5/284 604/83 |
| 2009/0171192 | A1 * | 7/2009 | Patrick | A61M 19/00 600/424 |
| 2009/0204066 | A1 * | 8/2009 | Radmer | A61J 1/20 604/86 |
| 2010/0106138 | A1 * | 4/2010 | Chavarria | A61B 17/00491 604/518 |
| 2010/0114158 | A1 * | 5/2010 | Hattan | A61B 17/00491 606/214 |

(56) References Cited

U.S. PATENT DOCUMENTS

| | | | |
|---|---|---|---|
| 2010/0233246 A1* | 9/2010 | Sehl | A61L 24/043 424/443 |
| 2010/0331600 A1* | 12/2010 | Bae | A61J 1/2096 600/5 |
| 2011/0004143 A1* | 1/2011 | Beiriger | A61M 1/342 604/6.11 |
| 2011/0021905 A1* | 1/2011 | Patrick | A61B 8/00 600/424 |
| 2011/0049181 A1* | 3/2011 | Lutz | A61J 1/2096 222/137 |
| 2011/0098657 A1* | 4/2011 | Jennings | A61J 1/2096 604/198 |
| 2011/0104280 A1* | 5/2011 | Hnojewyj | A61B 17/0057 424/486 |
| 2011/0152758 A1* | 6/2011 | Matusch | A61J 1/2096 604/83 |
| 2011/0166595 A1 | 7/2011 | Vidlund et al. | |
| 2011/0282383 A1* | 11/2011 | Vidlund | A61B 17/0057 606/213 |
| 2011/0295198 A1* | 12/2011 | Buisson | A61M 5/16804 604/83 |
| 2012/0114716 A1* | 5/2012 | Beals | A61K 9/0024 424/400 |
| 2012/0130386 A1* | 5/2012 | McKay | A61B 17/8825 606/94 |
| 2013/0006299 A1 | 1/2013 | Pipenhagen et al. | |
| 2013/0190808 A1 | 7/2013 | Tegels et al. | |
| 2013/0190812 A1 | 7/2013 | Vidlund | |
| 2013/0190813 A1 | 7/2013 | Tegels et al. | |
| 2013/0269299 A1* | 10/2013 | Parsonage | B65B 1/02 53/476 |
| 2014/0135831 A1* | 5/2014 | White | A61B 17/00491 606/214 |

OTHER PUBLICATIONS

U.S. Appl. No. 13/770,586, filed Feb. 19, 2013.
U.S. Appl. No. 13/770,714, filed Feb. 19, 2013.

* cited by examiner

SEALANT STORAGE, PREPARATION, AND DELIVERY SYSTEMS AND RELATED METHODS

RELATED APPLICATION

This claims the benefit of U.S. Provisional Application No. 61/692,859, filed 24 Aug. 2012, which is hereby incorporated by reference herein in its entirety.

TECHNICAL FIELD

The present disclosure relates generally to methods and systems for storing, preparing, and delivering sealant for sealing tissue punctures, and more particularly, to methods and systems for storing bioadhesive sealant components, for preparing bioadhesive sealant precursors, for preparing bioadhesive sealants, and for delivering bioadhesive sealants.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one primary problem is insuring a complete seal of the puncture. One technique includes the use of a bioadhesive sealant material to seal the puncture. Some types of bioadhesive sealant materials must be activated prior to use, and should be activated just prior to use in order to avoid premature activation of the bioadhesive sealant material. The handling and activation of bioadhesive sealant materials for use in vascular and other tissue puncture closure applications present a number of challenges, particularly when using bioadhesive sealant components that have a relatively short set time.

SUMMARY

One aspect of the present disclosure relates to bioadhesive sealant storage and preparation systems comprising a plurality of containers and an adapter. The plurality of containers comprises a first container having a first bioadhesive sealant component therein, and a second container having a second bioadhesive sealant component therein. The adapter comprises a manifold comprising a plurality of channels formed therein, an inlet region configured to connect to the plurality of containers and facilitate fluid communication between each container of the plurality of containers and a respective channel of the plurality of channels, and an outlet region configured to connect to at least one syringe and provide fluid communication between the at least one syringe and the plurality of channels.

The inlet region of the adapter may further include a receptacle configured to bias the plurality of containers to a first position, and to release the plurality of containers to a second position in response to an applied force. The plurality of containers may be separated from the manifold and be prevented from being in fluid communication with the plurality of channels when positioned in the first position. Additionally, the plurality of containers may each be proximate to the manifold and may each be in fluid communication with a respective channel of the plurality of channels when positioned in the second position.

The bioadhesive sealant storage and preparation system may further include a plurality of needles positioned at the inlet region of the adapter, each needle of the plurality of needles in fluid communication with a respective channel of the plurality of channels. Additionally, each container of the plurality of containers may comprise a septum. The bioadhesive sealant component of the first container may be stored at a first pressure and the second bioadhesive sealant component of the second container may be stored at a second pressure, the second pressure being greater than the first pressure. The bioadhesive sealant component of the first container may be stored in a vacuum condition. The bioadhesive sealant component of the first container may comprise a powder, and wherein the second bioadhesive sealant component of the second container may comprise a liquid.

A first channel of the plurality of channels may be positioned and configured for fluid communication with the bioadhesive sealant component of the first container. A second channel of the plurality of channels may be positioned and configured for fluid communication with the second bioadhesive sealant component of the second container when the plurality of containers are positioned in the second position. Additionally, the first channel may be in fluid communication with the second channel. The at least one syringe may comprise a double barrel syringe. The double barrel syringe may be configured to couple to the outlet region of the adapter, and to receive the bioadhesive sealant component of the first container and the second bioadhesive sealant component of the second container into a first barrel through a channel of the plurality of channels of the manifold. Additionally, the double barrel syringe may be configured to receive a third bioadhesive sealant component into a second barrel through another channel of the plurality of channels of the manifold. The bioadhesive sealant component of the first container may comprise at least one of polyethylene glycol and a thiol, and wherein the second bioadhesive sealant component of the second container may comprise an acrylate.

An additional aspect, which may be combined with other aspects herein, relates to bioadhesive sealant storage and preparation systems wherein the at least one syringe may comprise a double barrel syringe sized and configured to couple to the outlet region of the adapter. A first barrel of the double barrel syringe may comprise a third bioadhesive sealant component stored therein. The double barrel syringe may be configured to receive the first bioadhesive sealant component of the first container into the first barrel through a channel of the plurality of channels of the manifold, and to receive the second bioadhesive sealant component of the second container into a second barrel through another channel of the plurality of channels of the manifold.

The third bioadhesive sealant component may comprise at least one of polyethylene glycol and a thiol in a powder form. Additionally, the first bioadhesive sealant component of the first container may comprise an acrylate in liquid form, and the second bioadhesive sealant component of the second container may comprise an activator. The plurality of containers may further comprise a third container having a third bioadhesive sealant component therein. Additionally, the first container and the second container may be positioned and configured within a receptacle of the adapter to maintain the first bioadhesive sealant component and the second bioadhesive sealant component separated for storage and to allow the mixing of the first bioadhesive sealant component and the second bioadhesive sealant component in response to an applied force.

The adapter may further comprise a movable barrier positioned between the plurality of containers and the manifold. The movable barrier may be sized and configured to prevent fluid communication between the plurality of containers and the plurality of channels of the manifold when a force is applied and the movable barrier is positioned in a first position and to allow fluid communication between the plurality of containers and the plurality of channels of the manifold when the force is applied and the movable barrier is positioned in a second position. The bioadhesive sealant storage and preparation system may further include a syringe coupled to the outlet region of the adapter, and a pouch comprising a barrier separating a first region of the pouch from a second region of the pouch. Additionally, the syringe may be located in the first region of the pouch and the plurality of containers may be located within the second region of the pouch, which may be sterile.

An additional aspect of the present disclosure relates to tissue puncture closure systems comprising at least one syringe, a bioadhesive sealant storage and preparation system, and a delivery tube. The bioadhesive sealant storage and preparation system comprises a plurality of containers and an adapter. The plurality of containers comprises a first container having a first bioadhesive sealant component therein, and a second container having a second bioadhesive sealant component therein. The adapter comprises a manifold comprising a plurality of channels formed therein, an inlet region configured to connect to the plurality of containers and facilitate fluid communication between each container of the plurality of containers and a respective channel of the plurality of channels, and an outlet region configured to connect to the at least one syringe and provide fluid communication between the syringe and the plurality of channels for delivery of bioadhesive sealant components to the at least one syringe. The delivery tube is configured for insertion into a tissue puncture, a proximal end of the delivery tube is sized and configured to receive the at least one syringe, and a distal end of the delivery tube is configured to deliver a bioadhesive sealant from the at least one syringe to the tissue puncture.

The tissue puncture closure system may further include a pouch comprising a barrier separating a first region of the pouch from a second region of the pouch. Additionally, the syringe may be located in the first region of the pouch, and the plurality of containers may be located within the second region of the pouch, which may be sterile.

A further aspect of the present disclosure relates to methods of preparing a bioadhesive sealant. The methods comprise applying a force to a plurality of containers located at an inlet of an adapter, the plurality of containers comprising a first container having a first bioadhesive sealant component therein and a second container having a second bioadhesive sealant component therein, to facilitate fluid communication between the plurality of containers and a manifold of the adapter. The methods further comprise substantially simultaneously drawing the first bioadhesive sealant component and the second bioadhesive sealant component into a syringe coupled to an outlet region of the adapter through the manifold.

The method may include drawing the first bioadhesive sealant component into the second container. The method may include moving a movable barrier located between the plurality of containers and a manifold of the adapter prior to applying the force to the plurality of containers. The method may include maintaining the plurality of containers in a sealed region of a pouch separate from a sterile region wherein the syringe is located.

Another aspect of the present disclosure relates to methods of delivering sealant to a tissue puncture comprising applying a force to a plurality of containers located at an inlet of an adapter, the plurality of containers comprising a first container having a first bioadhesive sealant component therein and a second container having a second bioadhesive sealant component therein, to facilitate fluid communication between the plurality of containers and a manifold of the adapter. The methods further comprise substantially simultaneously drawing the first bioadhesive sealant component and the second bioadhesive sealant component into a syringe coupled to an outlet region of the adapter through the manifold, and uncoupling the syringe from the adapter. The methods additionally comprise, coupling the syringe to a proximal end of a delivery tube, inserting a distal end of the delivery tube into a tissue puncture, delivering a bioadhesive sealant from the syringe into the proximal end of the delivery tube, and conveying the bioadhesive sealant through the delivery tube to the distal end of the delivery tube and into the puncture.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

Throughout the drawings, identical reference numbers may designate similar, but not necessarily identical, elements.

DETAILED DESCRIPTION

Figure 1:
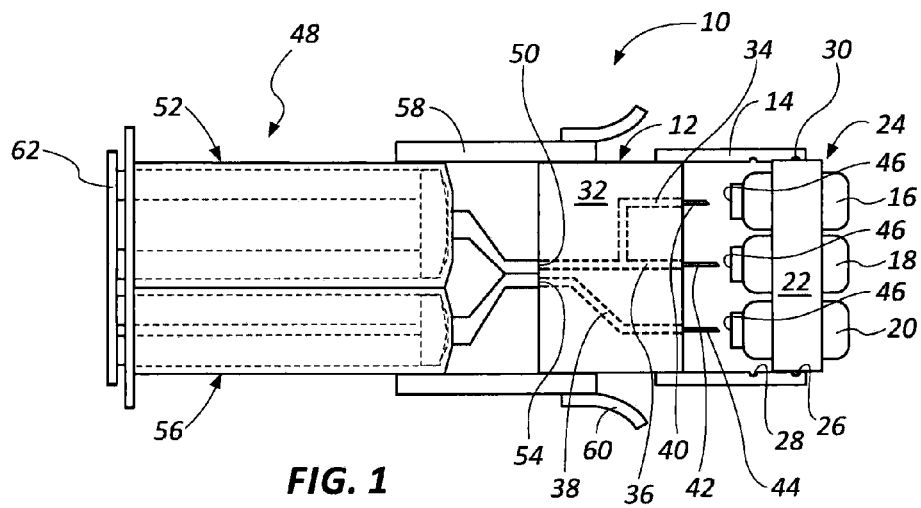
FIG. 1 is a side view of a bioadhesive sealant storage and preparation system according to an embodiment of the present disclosure.

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

As used in this specification and the appended claims, the terms "engage" and "engagable" are used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen", when referring to a bodily organ, refers to any open space or cavity in the bodily organ, especially in a blood vessel. The words "including" and "having," as well as their derivatives, as used in the specification, including the claims, have the same meaning as the word "comprising."

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

The sealants discussed herein may comprise a single component, or may comprise multiple sealant components that are mixed together. The multiple sealant components may further react together to form a crosslinked network. The sealant components may be naturally derived or synthetic. Some example synthetic components include polyethers such as polyethylene glycol, polypropylene glycol and polytetrahydrofuran. Other examples of synthetic components may include polyamine compositions such as polyvinylpyrrolidones, polyethylene imines and hydrogenated polyacrylonitriles. Other example sealant components include polyacrylic and methacrylic compounds such as polyacrylic acid. Example naturally derived components include protienaceous compositions such as albumin, collagen and polylysine. Other examples include carbohydrate compositions such polyhyaluronic acid. The sealant components may also contain reactive functional groups to promote chemical crosslinking. The sealant components may be cross-linked by any known method including, for example, condensation reactions, Michael addition, and free radical. Functional groups used for cross-linking may include, for example, thiols, acrylates, amines, succinimydyls and aldehydes, to name a few.

In some embodiments, as shown in FIG. 1, a bioadhesive sealant storage and preparation system 10 may include an adapter 12 comprising a receptacle 14 located at the inlet region thereof. The receptacle 14 may hold a plurality of containers 16, 18, 20 and restrict the motion of the plurality of containers 16, 18, 20 relative to the adapter 12. The plurality of containers 16, 18, 20 may be coupled together by a coupling device 22, such as one or more of a band (e.g., a polymer band), an adhesive, and a mechanical interference (e.g., a snap fit), to form a container unit 24, and thus may be moved relative to the adapter 12 as a cohesive unit.

Figure 2:
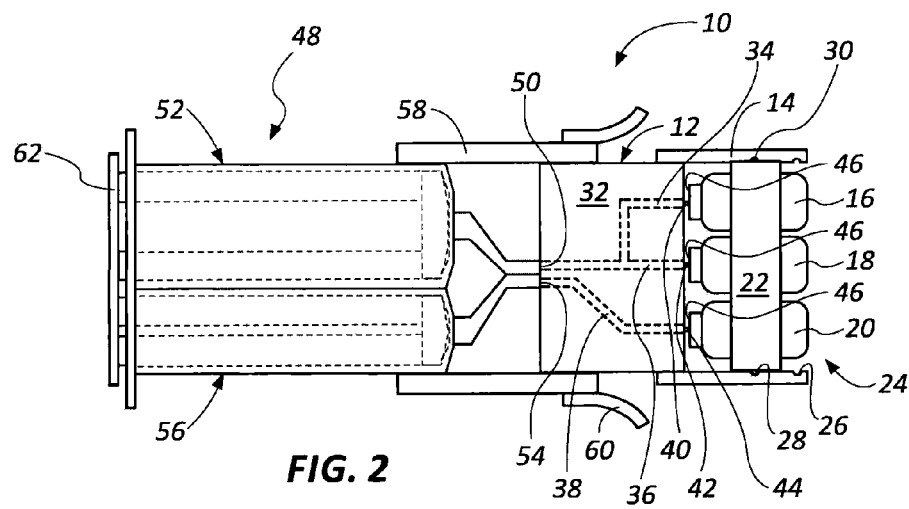
FIG. 2 is a side view of the bioadhesive sealant storage and preparation system of FIG. 1, wherein a plurality of containers of the bioadhesive sealant storage and preparation system have been moved to a second position.

The receptacle 14 may be configured to bias the plurality of containers 16, 18, 20 to a first position (as shown in FIG. 1) and configured to release the plurality of containers 16, 18, 20 to a second position in response to an applied force (as shown in FIG. 2). For example, the receptacle 14 may include a first recessed region 26 and a second recessed region 28, each sized to fit a protrusion 30 of the container unit 24. The first recessed region 26 may correspond to the first position and the second recessed region 28 may correspond to the second position. A region between the first and second recessed regions 26, 28 may provide resistance to movement of the container unit 24 from the first position (See FIG. 1) to the second position (See FIG. 2). For example, the region between the first and second recessed regions 26, 28 may provide a mechanical interference between the protrusion 30 of the container unit 24 and the receptacle 14 (e.g., the region may have an opening that is narrower than a width of the protrusion 30). Accordingly, deformation of one or both of the protrusion 30 and the receptacle 14 may be required for the passage of the container unit 24 from the first position to the second position. A force greater than a specific force threshold may be required for such deformation and thus to move the container unit 24 from the first position to the second position.

A manifold 32 of the adapter 12 includes a plurality of channels 34, 36, 38 formed therein extending from the inlet region of the adapter 12 to the outlet region of the adapter 12. The inlet region of the adapter 12 may include a plurality of needles 40, 42, 44, (e.g., hypodermic needles) extending from the manifold 32, each needle 40, 42, 44 in fluid communication with a respective channel 34, 36, 38 of the plurality of channels 34, 36, 38. A first needle 40 may be in fluid communication with a first channel 34, a second needle 42 may be in fluid communication with a second channel 36, and a third needle 44 may be in fluid communication with a third channel 38.

Each container 16, 18, 20 may be configured as a vial having a septum 46, such as a rubber septum. Accordingly, when the container unit 24 is positioned in the first position, each container 16, 18, 20 may be spaced away from the manifold 32, and the needles 40, 42, 44 extending from the manifold 32. When the container unit 24 is positioned in the second position, each needle 40, 42, 44 may extend through a septum 46 of a respective container 16, 18, 20 and provide fluid communication between each container 16, 18, 20 and a respective channel 34, 36, 38 of the manifold 32. The septum 46 of the first and second containers 16, 18 may be pierced substantially simultaneously, or the septum 46 of the second container 18 may be pierced prior to the septum 46 of the first container 16 being pierced (e.g., the second needle 42 may extend further than the first needle 40, and/or the first container 16 may be offset axially from the second container 18).

As shown in FIGS. 1 and 2, the first and second channels 34, 36 of the manifold 32 may be in fluid communication within the manifold 32, and may connect to a single channel extending to the outlet region of the adapter 12. The third channel 38 may extend through the manifold 32 from the inlet region to the outlet region of the adapter 12 and may be isolated from the first and second channels 34, 36. As such, when the container unit 24 is positioned in the second position (See FIG. 2), the first and second channels 34, 36 may provide a fluid flow path between the first container 16 and the second container 18. In one embodiment, the first bioadhesive sealant component of the first container 16 may comprise a powder, such as a powder comprising one or more of polyethylene glycol and a thiol, and the second bioadhesive sealant component of the second container 18 may comprise a liquid, such as a liquid comprising an acrylate.

The first bioadhesive sealant of the first container 16 may be stored at a first pressure and the second bioadhesive sealant of the second container 18 may be stored at a second pressure, the second pressure being greater than the first pressure. For example, the first bioadhesive sealant of the first container 16 may be stored at a pressure near ambient pressure (e.g., an absolute pressure of about 101 kPa) or above and the second bioadhesive sealant of the second container 18 may be stored in a near vacuum condition (e.g., at an absolute pressure near zero kPa). Accordingly, when the container unit 24 is positioned in the second position and the first and second containers 16, 18 are provided a fluid flow path therebetween via the first and second channels 34, 36, the pressure difference between the first container 16 and second container 18 may cause the second bioadhesive sealant component to flow from the second container 18 to the first container 16.

A syringe 48 configured to couple to the outlet end of the adapter 12 may be a double barrel syringe including a first opening 50 to a first barrel 52 and a separate second opening 54 to a second barrel 56. The syringe 48 may be coupled to the adapter 12 and held in place by a locking device 58, such as mating threads (not shown), or a latch comprising press tabs 60. When the syringe 48 is coupled to the outlet region of the adapter 12, the first opening 50 of the syringe 48 may provide fluid communication between the first and second channels 34, 36 of the manifold 32 and the first barrel 52 of the syringe 48, and the second opening 54 of the syringe 48 may provide fluid communication between the third channel 38 of the manifold 32 and the second barrel 56 of the syringe 48. Accordingly, when plungers 62 of the syringe 48 are drawn out (See FIG. 3), expanding the chambers of the first and second barrels 52, 56, respectively, the first and second bioadhesive components may flow from the first container 16 through the first channel 34, and optionally from the second container 18 through the second channel 36, to the first barrel 52 of the syringe 48.

Additionally, the third bioadhesive sealant component (e.g., an activator known to those skilled in the art), may flow from the third container 20 through the third channel 38 of the manifold 32 and into the second barrel 56 of the syringe 48. After the plungers 62 of the syringe 48 have been drawn out (See FIG. 3), the first barrel 52 of the syringe 48 may be filled with a bioadhesive sealant precursor comprising the combined first and second bioadhesive components and the second barrel 56 of the syringe 48 may be filled with an activator comprising the third bioadhesive component.

The locking device 58 may then be unlocked (e.g., the press tabs 60 of the latch may be pressed) and the syringe 48 may be uncoupled from the adapter 12 to be utilized with a delivery tube to administer a bioadhesive sealant comprising the bioadhesive sealant precursor and the activator to a tissue puncture (See FIGS. 11-14).

Figure 4:
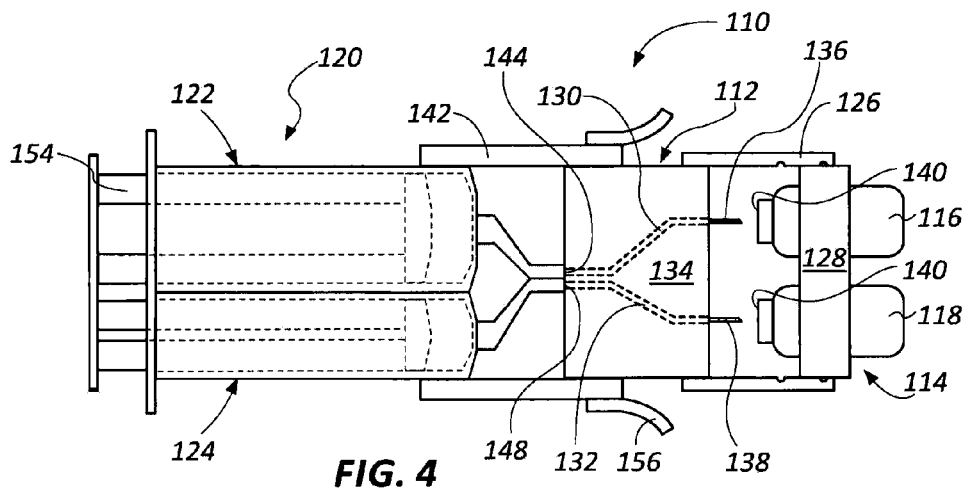
FIG. 4 is a side view of a bioadhesive sealant storage and preparation system including a container unit comprising two containers of bioadhesive components, according to another embodiment of the present disclosure.

In additional embodiments, a bioadhesive sealant storage and preparation system 110 may include an adapter 112 sized and configured to receive a container unit 114 comprising two containers 116, 118 of bioadhesive components at the inlet region of the adapter 112, as shown FIG. 4. A first container 116 of the container unit 114 may have a first bioadhesive sealant component therein and the second container 118 may have a second bioadhesive sealant component therein, wherein the second bioadhesive sealant component is different than the first bioadhesive sealant component. Additionally, the bioadhesive sealant storage and preparation system 110 may include a syringe 120, such as a double barrel syringe, sized and configured to couple to the outlet region of the adapter 112. A first barrel 122 of the syringe 120 may comprise a third bioadhesive sealant component stored therein, wherein the third bioadhesive sealant component is different than the first and second bioadhesive sealant components.

A second barrel 124 of the syringe 120 may include the same bioadhesive sealant component as stored in the second container 118 (i.e., the second bioadhesive sealant component) stored therein, or the second barrel 124 may be substantially empty. For example, the first bioadhesive sealant component within the first container 116 may be a liquid comprising an acrylate, the second bioadhesive component of the second container 118 may be a liquid comprising an activator, and the third bioadhesive component of the first barrel 122 of the syringe 120 may be a powder comprising at least one of polyethylene and a thiol.

Figure 3:
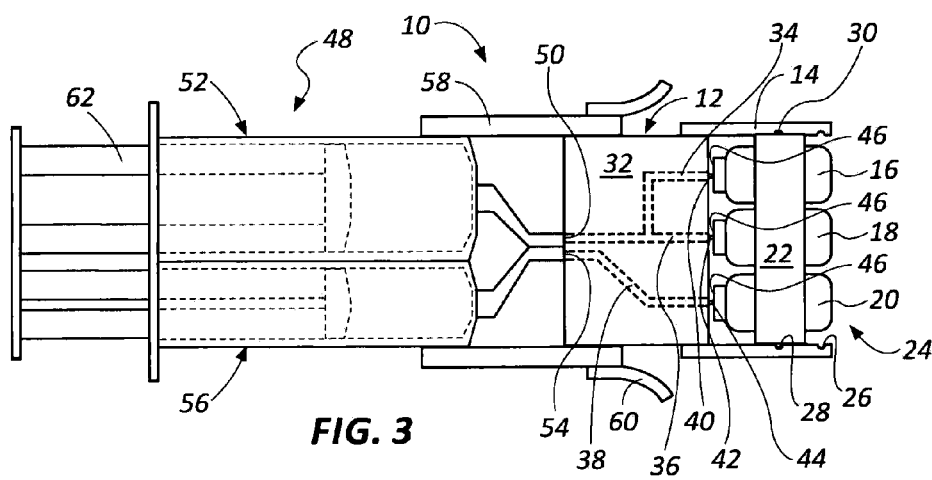
FIG. 3 is a side view of the bioadhesive sealant storage and preparation system of FIG. 2, wherein bioadhesive sealant components have been withdrawn from the plurality of containers into a syringe.
Figure 5:
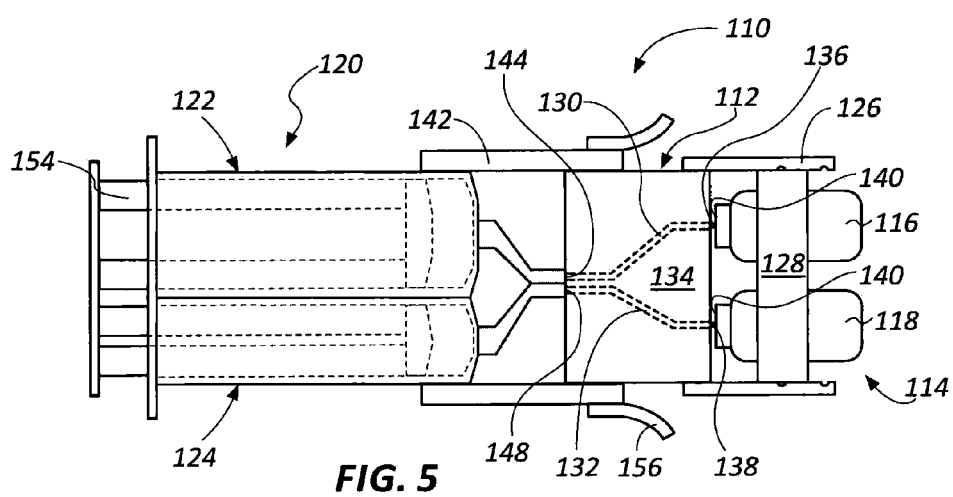
FIG. 5 is a side view of the bioadhesive sealant storage and preparation system of FIG. 4, wherein the container unit has been moved to a second position.
Figure 6:
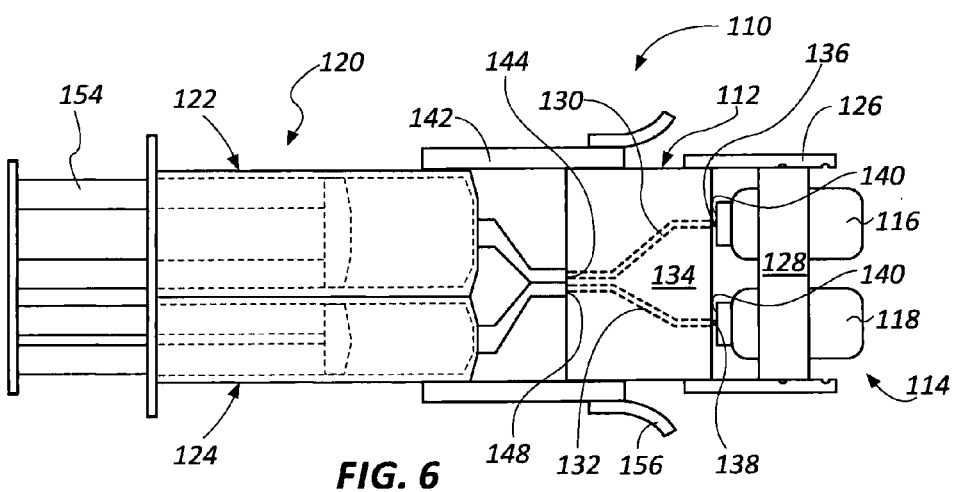
FIG. 6 is a side view of the bioadhesive sealant storage and preparation system of FIG. 5, wherein the bioadhesive sealant components of the two containers have been withdrawn from the containers into a syringe.

Similar to the adapter 12 described with reference to FIGS. 1-3, the adapter 112 shown in FIGS. 4-6 includes a receptacle 126 that may hold the container unit 114 and restrict the motion of the containers 116, 118 relative to the adapter 112. The receptacle 126 may be configured to bias the first and second containers 116, 118 to a first position (as shown in FIG. 4) and configured to release the plurality of containers 116, 118 to a second position in response to an applied force (as shown in FIG. 5). The container unit 114 may comprise the first and second containers 116, 118 coupled together by a coupling device 128, such as one or more of a band (e.g., a polymer band), an adhesive, and a mechanical interference (e.g., a snap fit). Thus, the first and second containers 116, 118 may be moved relative to the adapter 112 as a cohesive unit. Optionally, the first and second containers 116, 118 may not be coupled together by a coupling device 128 and may be movable separately relative to the adapter 112. Coupling the first and second containers 116, 118 together may reduce the number of steps required to operate the bioadhesive sealant storage and preparation system 110, thus facilitating a quick and effective operation of the bioadhesive sealant storage and preparation system 110.

The adapter 112 may include a first channel 130 and a second channel 132 extending from the inlet region to the outlet region of the adapter 112 through a manifold 134. Additionally, the adapter 112 may include a first needle 136 and a second needle 138 at the inlet region of the manifold 134, wherein the first needle 136 is in fluid communication with the first channel 130 and the second needle 138 is in fluid communication with the second channel 132. When the first and second containers 116, 118 are moved from the first position (See FIG. 4) to the second position (See FIG. 5), the first needle 136 may pierce a septum 140 of the first container 116 and the second needle 138 may pierce a septum 140 of the second container 118. Accordingly, the first needle 136 may provide a fluid flow path between the first container 116 and the first channel 130 of the manifold 134 and the second needle 138 may provide a fluid flow path between the second container 118 and the second channel 132 of the manifold 134. The septum 140 of the first and second containers 116, 118 may be pierced substantially simultaneously, or the septum 140 of the first container 116 may be pierced prior to the septum 140 of the second container 118 being pierced (e.g., the first needle 136 may extend further than the second needle 138, and/or the first container 116 may be offset axially from the second container 118).

The syringe 120 may be coupled to the outlet region of the adapter 112 and held in place by a locking device 142. When the syringe 120 is coupled to the outlet region of the adapter 112, a first opening 144 of the syringe 120 may provide fluid communication between the first channel 130 of the manifold 134 and the first barrel 122 of the syringe 120, and the second opening 148 of the syringe 120 may provide fluid communication between the second channel 132 of the manifold 134 and the second barrel 124 of the syringe 120. Accordingly, when plungers 154 of the syringe 120 are drawn out (See FIG. 6), thereby expanding the chambers of the first and second barrels 122, 124, respectively, the first bioadhesive sealant component may flow from the first container 116 through the first channel 130 of the manifold 134 to the first barrel 122 of the syringe 120 and mix with the third bioadhesive sealant component stored in the first barrel 122. Additionally, the second bioadhesive sealant component (e.g., an activator), may flow from the second container 118 through the second channel 132 of the manifold 134 and into the second barrel 124 of the syringe 120, and may optionally mix with additional second bioadhesive sealant component stored in the second barrel 124. After the plungers 154 of the syringe 120 have been drawn out (See FIG. 6), the first barrel 122 of the syringe 120 may be filled with a bioadhesive sealant precursor comprising the combined first and second bioadhesive components and the second barrel 124 of the syringe 120 may be filled with an activator comprising the third bioadhesive component.

The locking device 142 may then be unlocked (e.g., press tabs 156 of a latch may be pressed) and the prepared syringe 120 may be uncoupled from the adapter 112 to be utilized with a delivery tube to administer a bioadhesive sealant comprising the bioadhesive sealant precursor and the activator to a tissue puncture (See FIGS. 11-14).

Figure 7:
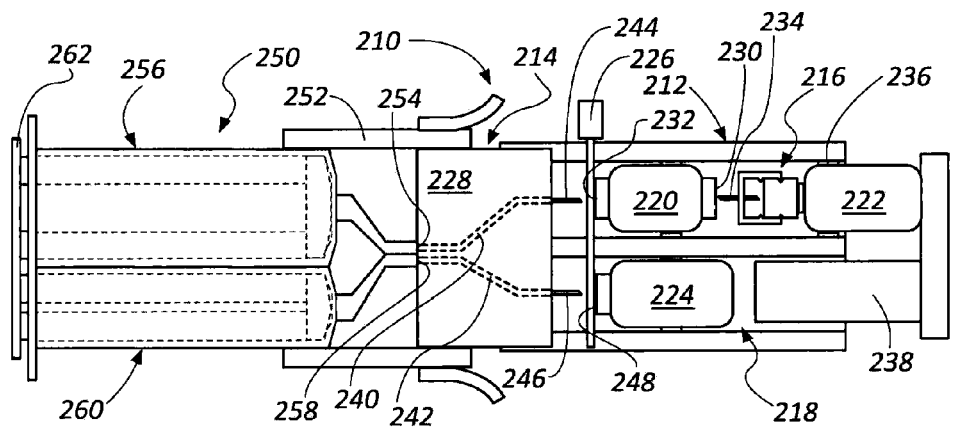
FIG. 7 is a side view of a bioadhesive sealant storage and preparation system including a cartridge containing a plurality of containers of bioadhesive components, according to an additional embodiment of the present disclosure.

In further embodiments, such as shown in FIG. 7, a bioadhesive sealant storage and preparation system 210 may include a bioadhesive sealant component retaining device 212 attached to an adapter 214. The bioadhesive sealant component retaining device 212 may include a first storage region 216 and a second storage region 218, wherein the first storage region 216 contains a first container 220 having a bioadhesive sealant component therein and a second container 222 contains a second bioadhesive sealant component therein. The second storage region 218 may contain a third container 224 having a third bioadhesive sealant component therein. Each of the first, second and third containers 220, 222, 224 may be retained in a fixed position relative to each other, and relative to the adapter 214, by the bioadhesive sealant component retaining device 212. The bioadhesive sealant component retaining device 212 may further include a movable barrier 226 positioned between the plurality of containers 220, 222, 224 and a manifold 228 of the adapter 214. For example, the bioadhesive sealant component retaining device 212 may be a cartridge for holding separate first, second and third vials containing respective first, second and third bioadhesive components. The first storage region 216 comprises a first chamber of the cartridge and the second storage region 218 comprises a second chamber of the cartridge, as shown in FIG. 7.

Figure 8:
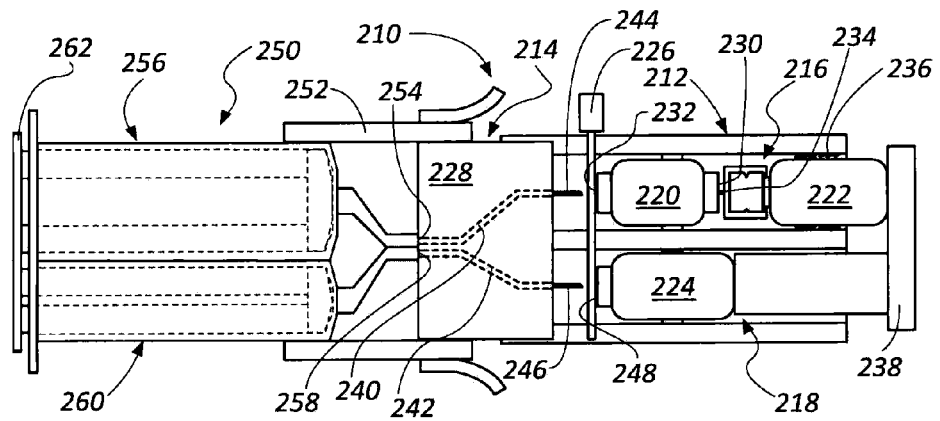
FIG. 8 is a side view of the bioadhesive sealant storage and preparation system of FIG. 7, wherein a second container within the cartridge has been moved to a second position.

The first container 220 may include a first septum 230 and an opposing second septum 232. A needle 234 may be positioned between the second container 222 and the first septum 230 of the first container 220. A securing device 236, such as one or more of a mechanically locking tab, an adhesive, and a frangible material, may maintain the position of the second container 222 relative to the first container 220 and the first and second containers 220, 222 may be held separate until a force is applied to the second container 222, such as by pressing on a surface of a plunger 238, and the securing device 236 is caused to release the second container 222. Upon the force being applied to the second container 222 via the plunger 238, the second container 222 may be released by the securing device 236 and the second container 222 may be moved to a second position, proximate to the first container 220, as shown in FIG. 8. As the second container 222 is moved to the second position, the needle 234, or other similar structure, may pierce the septum 230 of the first and second containers 220, 222 and provide fluid communication between the first and second containers 220, 222.

In one embodiment, the first bioadhesive sealant component of the first container 220 may comprise a powder, such as a powder comprising one or more of polyethylene glycol and a thiol. The second bioadhesive sealant component of the second container 222 may comprise a liquid, such as a liquid comprising an acrylate. The first bioadhesive sealant of the first container 220 may be stored at a first pressure and the second bioadhesive sealant of the second container 222 may be stored at a second pressure, wherein the second pressure is greater than the first pressure. For example, the first bioadhesive sealant of the first container 220 may be stored at a pressure near ambient pressure (e.g., an absolute pressure of about 101 kPa) or above and the second bioadhesive sealant of the second container 222 may be stored in a near vacuum condition (e.g., at an absolute pressure near zero kPa). Accordingly, when the second container 222 is positioned in the second position (See FIG. 8) and the first and second containers 220, 222 are provided a fluid flow path therebetween via the needle 234, the pressure difference between the first container 220 and second container 222 may cause the second bioadhesive sealant component to flow from the second container 222 to the first container 220.

The adapter 214 may include a first channel 240 and a second channel 242 extending from the inlet region to the outlet region of the adapter 214 through the manifold 228. Additionally, the adapter 214 may include a first needle 244 and a second needle 246 at the inlet region of the manifold 228, wherein the first needle 244 is in fluid communication with the first channel 240 and the second needle 246 is in fluid communication with the second channel 242.

Figure 9:
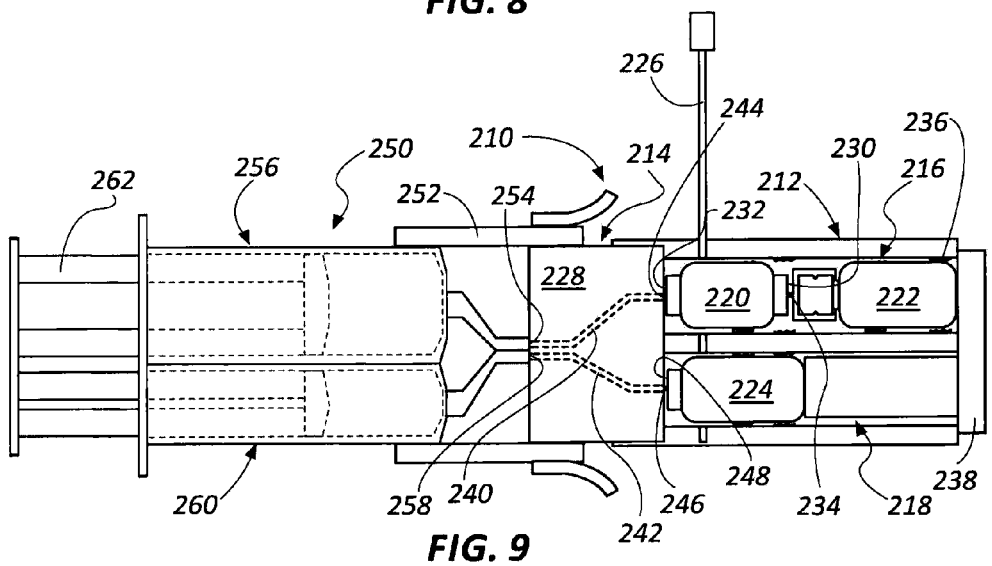
FIG. 9 is a side view of the bioadhesive sealant storage and preparation system of FIG. 8, wherein bioadhesive sealant components have been withdrawn from the plurality of containers within the cartridge into a syringe.

After the first and second bioadhesive sealant components have mixed together in the first container 220, the movable barrier 226 may be displaced or removed to provide an unobstructed path between the first and third containers 220, 224 and the inlet region of the adapter 214. Then a force may be applied to the plurality of containers 220, 222, 224 via the plunger 238 to cause the first and third containers 220, 224 to move toward the inlet region of the adapter 214, as shown in FIG. 9. Accordingly, the first needle 244 may pierce the second septum 232 of the first container 220 and the second needle 246 may pierce a septum 248 of the third container 224. The first needle 244 may provide a fluid flow path between the first container 220 and the first channel 240 of the manifold 228, and the second needle 246 may provide a fluid flow path between the third container 224 and the second channel 242 of the manifold 228.

Figure 10:
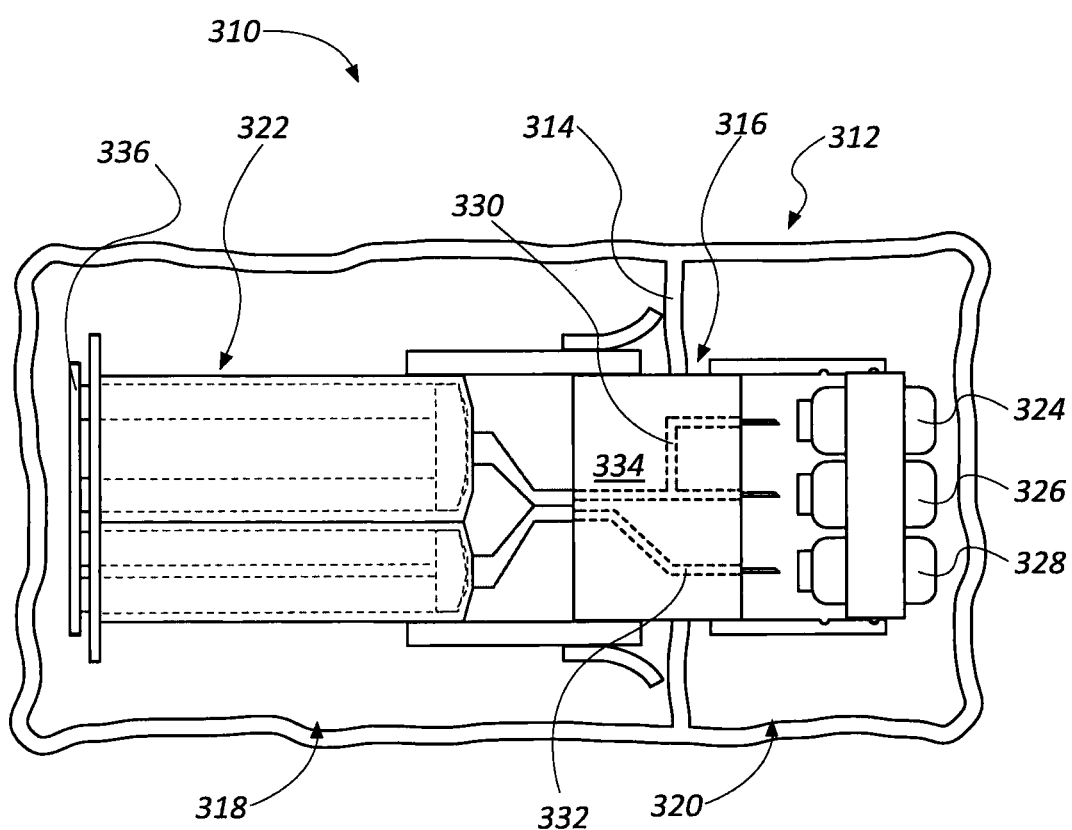
FIG. 10 is a side view of a bioadhesive sealant storage and preparation system, such as shown in FIG. 1, enclosed within a pouch, according to an embodiment of the present disclosure.

A syringe 250 may be coupled to the outlet region of the adapter 214 and held in place by a locking device 252. When the syringe 250 is coupled to the outlet region of the adapter 214, a first opening 254 of the syringe 250 may provide fluid communication between the first channel 240 of the manifold 228 and a first barrel 256 of the syringe 250. The second opening 258 of the syringe 250 may provide fluid communication between the second channel 242 of the manifold 228 and a second barrel 260 of the syringe 250. Accordingly, when plungers 262 of the syringe 250 are drawn out (See FIG. 10), thereby expanding chambers of the first and second barrels 256, 260, respectively, the first and second bioadhesive sealant components may flow from the first container 220 through the first channel 240 of the manifold 228 to the first barrel 256 of the syringe 250. Additionally, the third bioadhesive sealant component (e.g., an activator), may flow from the third container 224 through the second channel 242 of the manifold 228 and into the second barrel 260 of the syringe 250. After the plungers 262 of the syringe 250 have been drawn out (FIG. 10), the first barrel 256 of the syringe 250 may be filled with a bioadhesive sealant precursor comprising the combined first and second bioadhesive components, and the second barrel 260 of the syringe 250 may be filled with an activator comprising the third bioadhesive component.

The locking device 252 may then be unlocked (e.g., the tabs of the latch may be pressed) and the syringe 250 may be uncoupled from the adapter 214 to be utilized with a delivery tube to administer a bioadhesive sealant comprising the bioadhesive sealant precursor and the activator to a tissue puncture (See FIGS. 11-14).

Figure 11:
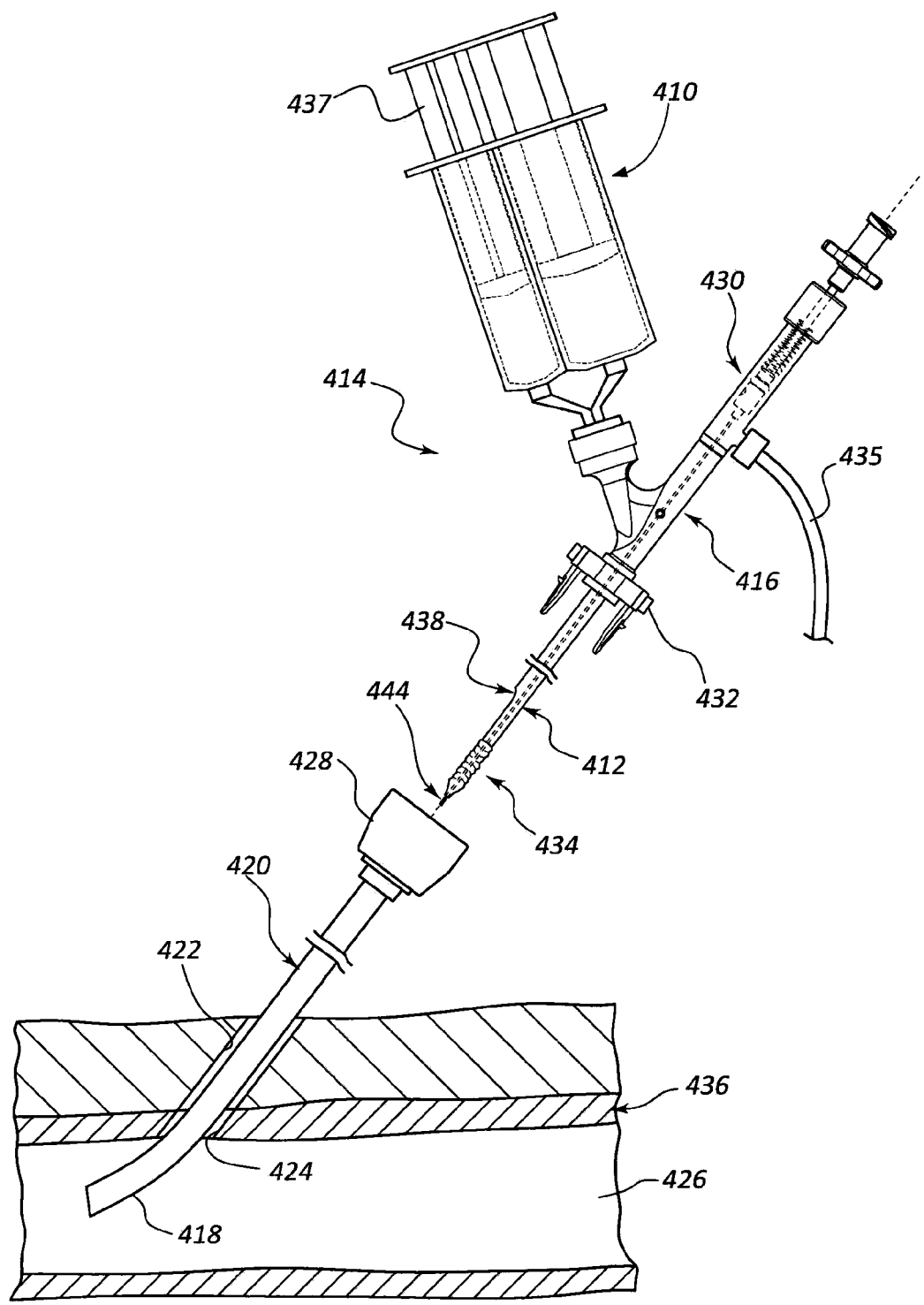
FIGS. 11-14 illustrate the use of a syringe prepared utilizing a bioadhesive sealant and storage system, such as shown in FIGS. 1, 4, and 7, with a vascular closure device and a sheath to seal closed a vessel puncture, according to an embodiment of the present disclosure.

In some embodiments, a bioadhesive sealant storage and preparation system 310, which may be configured as a bioadhesive storage and preparation system 10, 110, 210 as described with reference to FIGS. 1, 4, and 7, respectively, may further comprise a surrounding pouch 312, as shown in FIG. 11. The pouch 312 may include a barrier 314 attached to an adapter 316, wherein the barrier 314 separates a first region 318 of the pouch 312 from a second region 320 of the pouch 312. The first region 318 of the pouch 312 may be sterile, and a syringe 322 may be located in the first region 318 of the pouch 312. A plurality of containers 324, 326, 328 may be located within the second region 320 of the pouch 312, separated from the sterile first region 318 by the barrier 314.

As in the embodiments described with reference to FIGS. 1-10, the plurality of containers 324, 326, 328 may include a first container 324 having a first bioadhesive component therein, a second container 326 having a second bioadhesive component therein, and optionally, a third container 328 having a third bioadhesive component therein. The pouch 312 may comprise a flexible material, such as a polymer, and may be transparent or include transparent regions. This may enable the syringe 322 to be prepared with bioadhesive sealant components from the plurality of containers 324, 326, 328 and removed from the pouch 312 without ever opening the second region 320 of the pouch 312, which have the plurality of containers 324, 326, 328 held therein. Accordingly, the plurality of containers 324, 326, 328 may be unsterile, yet may not contaminate a sterile environment, such as a sterile operating room or a sterile preparation room, as the plurality of containers 324, 326, 328 may remain sealed within the second region 320 of the pouch 312.

In operation, the bioadhesive preparation and storage system 310 may be provided within the pouch 312. The syringe 322 located in the first region 318 (i.e., the sterile region) of the pouch 312 may be coupled to an outlet region of the adapter 316. Next, a force may be applied to the plurality of containers 324, 326, 328 located within the second region 320 of the pouch 312 and at an inlet region of the adapter 316 to provide fluid communication between the plurality of containers 324, 326, 328 and the syringe 322 via channels 330, 332 within a manifold 334 of the adapter 316. Then, plungers 336 of the syringe 322 may be drawn out to substantially simultaneously draw the first bioadhesive sealant component, the second bioadhesive sealant component, and, optionally, the third bioadhesive sealant component, into the syringe 322.

The prepared syringe 322 may then be uncoupled from the adapter 316 and removed from the first region 318 of the pouch 312 to be utilized with a delivery tube to administer a bioadhesive sealant comprising the bioadhesive sealant precursor and the activator to a tissue puncture (See FIGS. 11-14).

As shown in FIG. 11, a prepared syringe 410, which may be a syringe 48, 120, 250, 322 prepared as described with reference to FIGS. 1-10, may be coupled to a proximal end of a delivery tube 412 of a vascular closure device 414 via a manifold 416, as shown in FIG. 11.

As further shown in FIG. 11, a distal end 418 of a sheath 420 may be advanced through a tissue tract 422 and a vessel puncture 424 and into a vessel lumen 426. The vascular closure device 414 may be aligned with an opening into a hub 428 of the sheath 420 for insertion into the sheath. Prior to inserting the vascular closure device 414 into the sheath 420, the delivery tube 412 may be connected to the manifold 416, and a balloon location device 430 may be advanced through the manifold 416 and delivery tube 412 and connected to a proximal end of the manifold 416.

Figure 12:
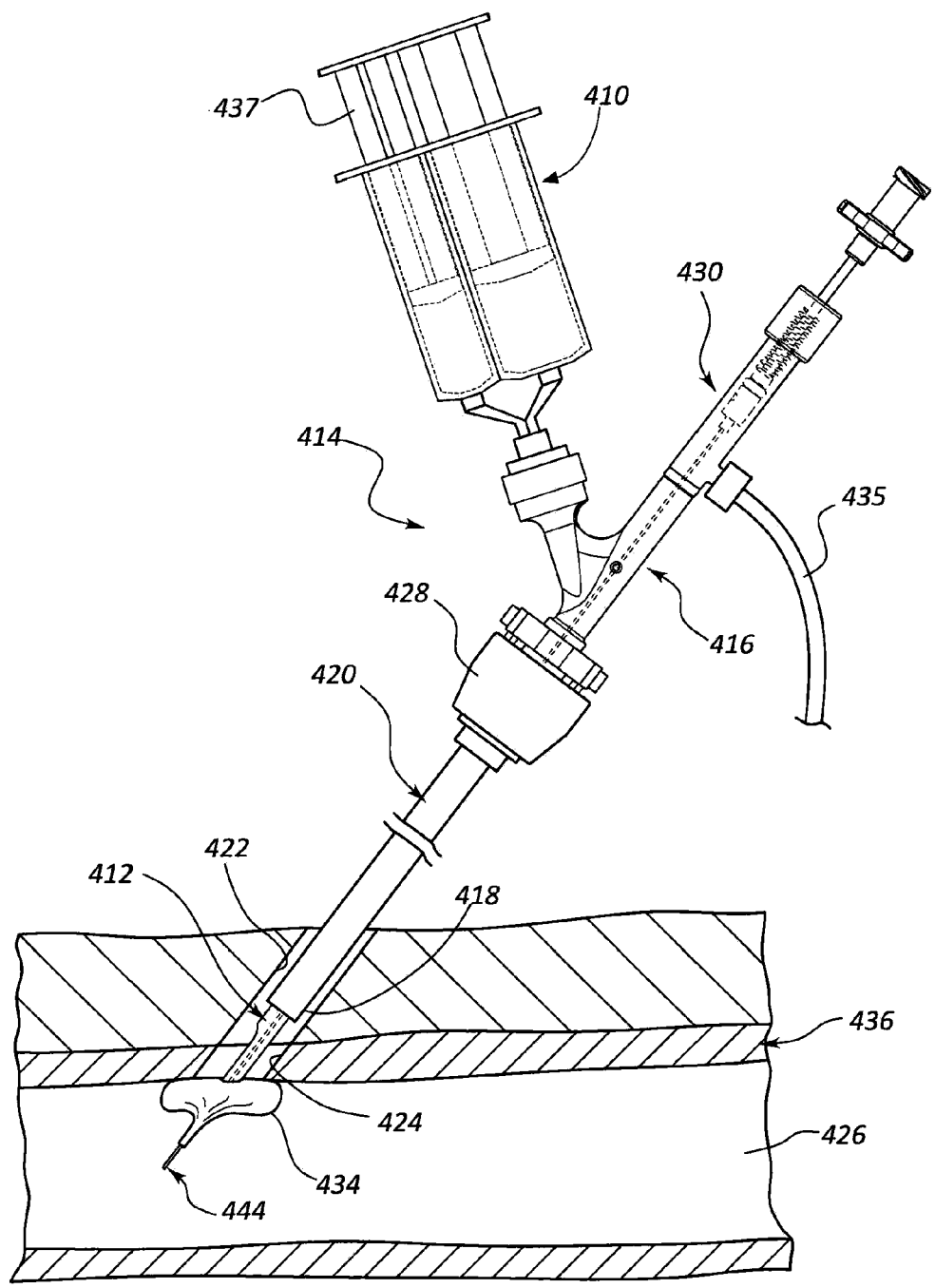

Referring to FIG. 12, the delivery tube 412 may be advanced through the sheath 420 and a latch 432 may be connected to the hub 428 of the sheath 420. A balloon 434 may be inflated by delivering a volume of inflation fluid from an inflation fluid source 435, through a housing of the balloon location device 430, through a first lumen of the delivery tube 412, and into the balloon 434. The vascular closure device 414 and sheath 420 may then be retracted (e.g., withdrawn proximally) to bring the inflated balloon 434 into contact with an inner surface of the vessel 436 adjacent to the vessel puncture 424. Accordingly, the inflated balloon 434 may provide a temporary seal with the vessel 436 to limit blood flow through the vessel puncture 424 from within the vessel lumen 426.

Figure 13:
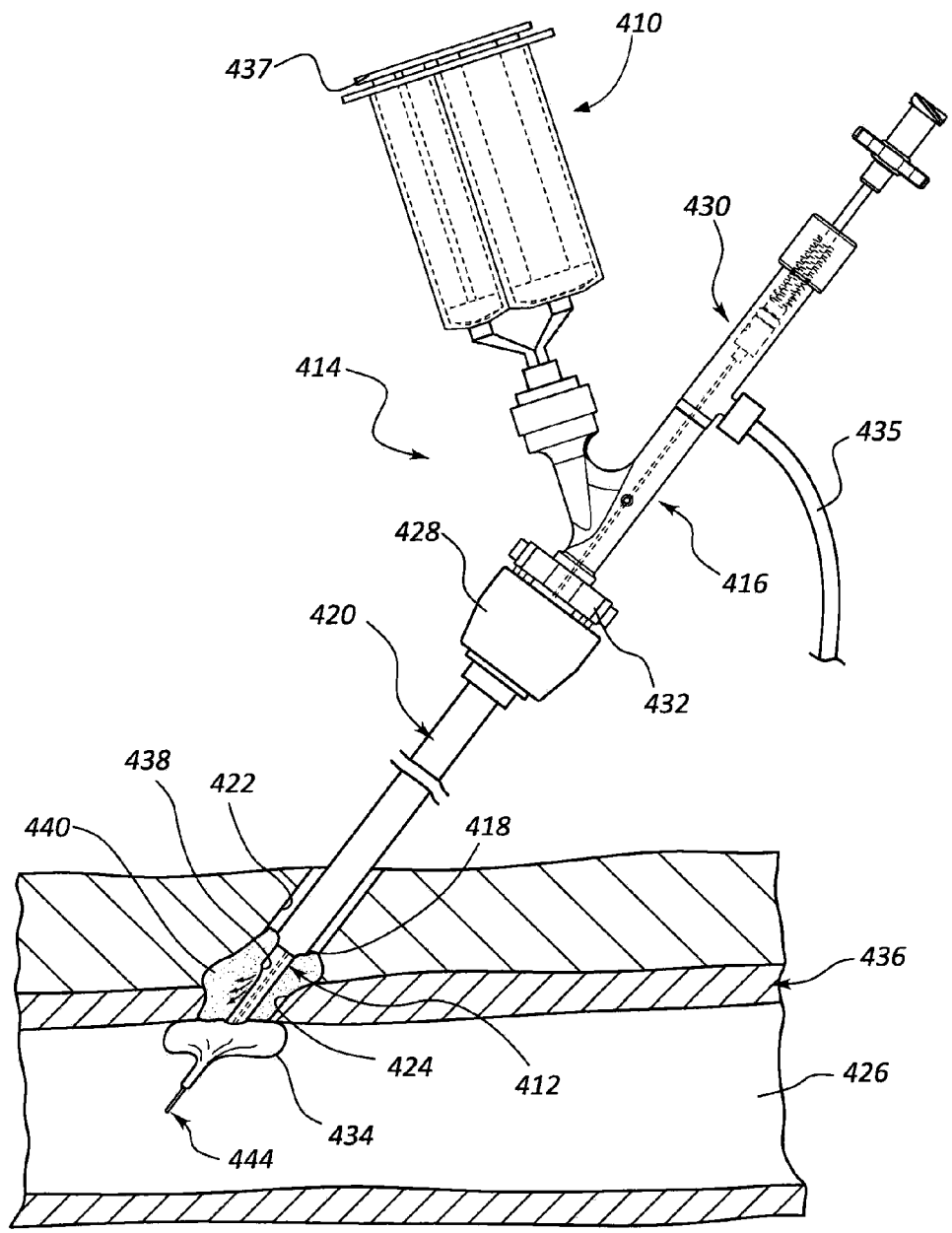

Referring to FIG. 13, plungers 437 of the syringe 410 may then be advanced to inject a bioadhesive sealant precursor and activator into the manifold 416 to mix and provide a bioadhesive sealant. The bioadhesive sealant is then delivered through the manifold 416 and a second lumen of the delivery tube 412, and out a distal opening 438, to the vessel puncture 424 and tissue tract 422. The bioadhesive sealant may form a bioadhesive plug 440 that may seal closed the vessel puncture 424 and tissue tract 422 from outside of the vessel 436. The bioadhesive sealant forming the bioadhesive plug 440 may be allowed to at least partially cure into a solid or semi-solid state that limits movement of the bioadhesive sealant of the bioadhesive plug 440 into the vessel lumen 426 upon deflating the balloon 434.

Figure 14:
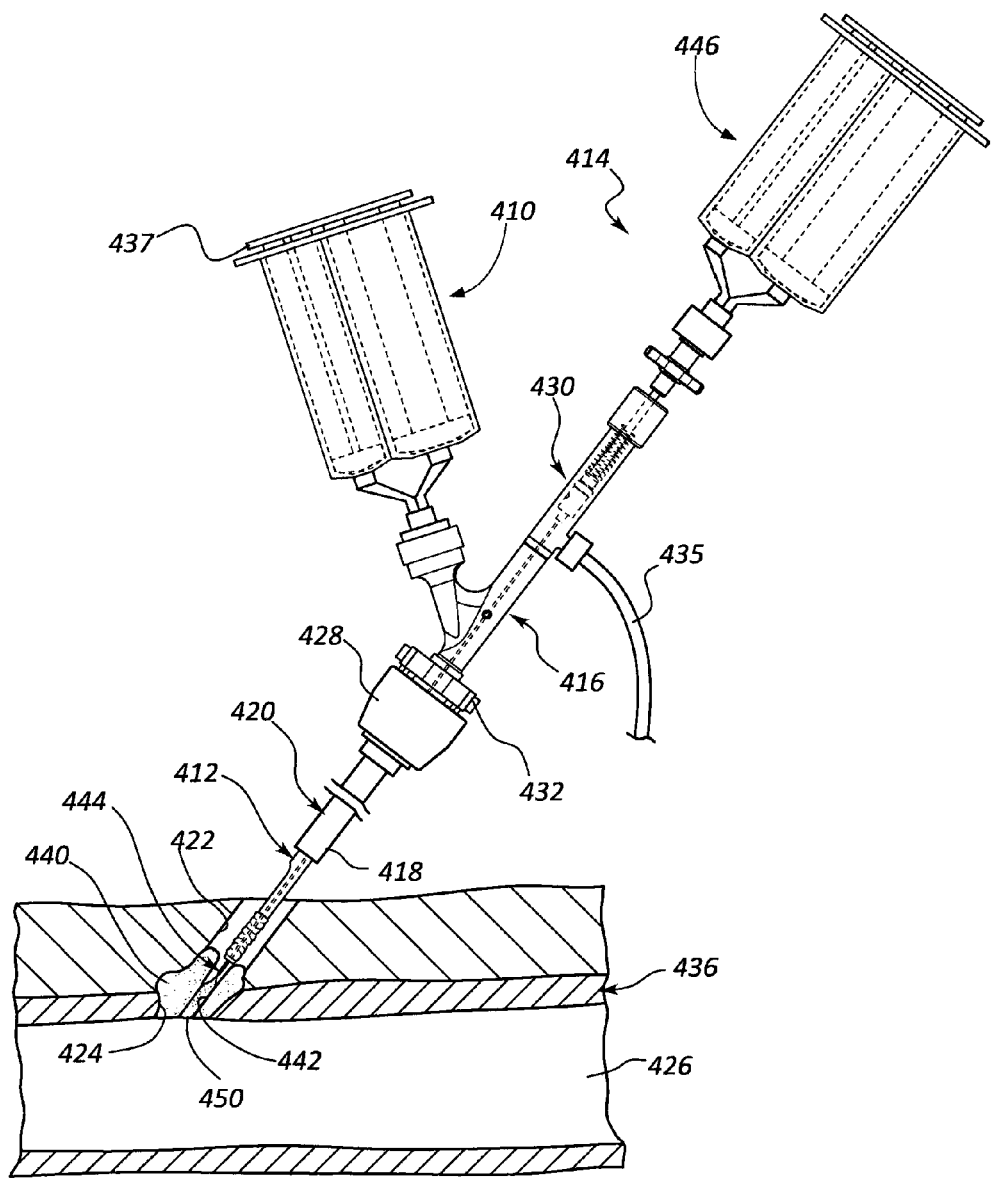

Referring to FIG. 14, the balloon 434 may then be deflated by withdrawing the inflation fluid through the first lumen of the delivery tube 412. The vascular closure device 414 and sheath 420 may then be further retracted or withdrawn, so that the delivery tube 412 may be positioned proximal to the bioadhesive plug 440. A tract 442 may be defined within the bioadhesive plug 440 after removal of the delivery tube 412. The tract 442 may be filled by delivering a second bioadhesive sealant via an inner tube 444. Accordingly, a second syringe 446 may be prepared with a bioadhesive precursor and activator, similar to the syringe 410, and may be connected to an inner tube 444 and operated to deliver a volume of second bioadhesive sealant through the inner tube 444 and into the tract 442. The second bioadhesive sealant may form into a second bioadhesive plug 450 within the tract 442 to provide further sealing of the vessel puncture 424.

After delivering the second bioadhesive sealant and forming the second bioadhesive plug 450, the entire vascular closure device 414 and sheath 420 may be removed from the tissue tract 422 and the sealing procedure may be complete.

The sealants and sealant components discussed herein may comprise a single component, or may comprise multiple sealant components that are mixed together. The multiple sealant components may further react together to form a cross-linked network. The sealant components may be naturally derived or synthetic. Some example synthetic components include polyethers such as polyethylene glycol, polypropylene glycol and polytetrahydrofuran. Other examples of synthetic components may include polyamine compositions such as polyvinylpyrrolidones, polyethylene imines and hydrogenated polyacrylonitriles. Other example sealant components include polyacrylic and methacrylic compounds such as polyacrylic acid. Example naturally derived components include protienaceous compositions such as albumin, collagen and polylysine. Other examples include carbohydrate compositions such polyhyaluronic acid. The sealant components may also contain reactive functional groups to promote chemical cross-linking. The sealant components may be cross-linked by any known method including, for example, condensation reactions, Michael addition, and free radical. Functional groups used for cross-linking may include, for example, thiols, acrylates, amines, succinimydyls and aldehydes, to name a few.

The preceding description has been presented only to illustrate and describe example embodiments of the invention. It is not intended to be exhaustive or to limit the invention to any precise form disclosed. Many modifications and variations are possible in light of the above teachings. It is intended that the scope of the invention be defined by the following claims.

What is claimed is:

1. A bioadhesive sealant storage and preparation system, comprising:
    a plurality of containers, the plurality of containers comprising:
        a first container having a first bioadhesive sealant component therein;
        a second container having a second bioadhesive sealant component therein;
    a coupling device coupling the plurality of containers together, the coupling device comprising a protrusion;
    an adapter movable relative to the coupling device, the adapter comprising:
        a manifold comprising a plurality of channels formed therein;
        an inlet region configured to connect to the plurality of containers and facilitate fluid communication between each container of the plurality of containers and a respective channel of the plurality of channels, the inlet region comprising a receptacle, the plurality of containers being movable between a first position at which the containers are connected to the receptacle and a second position at which the containers are connected to the receptacle, the plurality of containers being biased to the first position;
        a first recess formed in the receptacle and a second recess formed in the receptacle, wherein the protrusion of the coupling device is seated in the first recess when the plurality of containers are in the first position and the protrusion is seated in the second recess when the plurality of containers are in the second position;
        an outlet region configured to connect to at least one syringe and provide fluid communication between the at least one syringe and the plurality of channels.

2. The bioadhesive sealant storage and preparation system of claim 1, wherein the receptacle is configured to release the plurality of containers to a second position in response to an applied force, wherein the plurality of containers are separated from the manifold and are prevented from being in fluid communication with the plurality of channels when positioned in the first position, wherein the plurality of containers are each proximate to the manifold and are each in fluid communication with a respective channel of the plurality of channels when positioned in the second position.

3. The bioadhesive sealant storage and preparation system of claim 2, further comprising:
    a plurality of needles positioned at the inlet region of the adapter, each needle of the plurality of needles in fluid communication with a respective channel of the plurality of channels;
    wherein each container of the plurality of containers comprises a septum.

4. The bioadhesive sealant storage and preparation system of claim 3, wherein the at least one syringe comprises a double barrel syringe sized and configured to couple to the outlet region of the adapter, a first barrel of the double barrel syringe comprising a third bioadhesive sealant component stored therein, the double barrel syringe configured to receive the first bioadhesive sealant component of the first container into the first barrel through a channel of the plurality of channels of the manifold, to receive the second bioadhesive sealant component of the second container into a second barrel through another channel of the plurality of channels of the manifold.

5. The bioadhesive sealant storage and preparation system of claim 4:
    wherein the third bioadhesive sealant component comprises at least one of polyethylene glycol and a thiol in a powder form;
    wherein the first bioadhesive sealant component of the first container comprises an acrylate in liquid form;
    wherein the second bioadhesive sealant component of the second container comprises an activator.

6. The bioadhesive sealant storage and preparation system of claim 2, wherein the first bioadhesive sealant component of the first container is stored at a first pressure and the second bioadhesive sealant component of the second container is stored at a second pressure, the second pressure being greater than the first pressure.

7. The bioadhesive sealant storage and preparation system of claim 6, wherein the first bioadhesive sealant component of the first container is stored in a vacuum condition.

8. The bioadhesive sealant storage and preparation system of claim 7, wherein the first bioadhesive sealant component of the first container comprises a powder and wherein the second bioadhesive sealant component of the second container comprises a liquid.

9. The bioadhesive sealant storage and preparation system of claim 8:
wherein a first channel of the plurality of channels is positioned and configured for fluid communication with the first bioadhesive sealant component of the first container and a second channel of the plurality of channels is positioned and configured for fluid communication with the second bioadhesive sealant component of the second container when the plurality of containers are positioned in the second position;
wherein the first channel is in fluid communication with the second channel.

10. The bioadhesive sealant storage and preparation system of claim 9, wherein the at least one syringe comprises a double barrel syringe sized and configured to couple to the outlet region of the adapter, to receive the first bioadhesive sealant component of the first container and the second bioadhesive sealant component of the second container into a first barrel through a channel of the plurality of channels of the manifold, and to receive a third bioadhesive sealant component into a second barrel through another channel of the plurality of channels of the manifold.

11. The bioadhesive sealant storage and preparation system of claim 8, wherein the first bioadhesive sealant component of the first container comprises at least one of polyethylene glycol and a thiol, wherein the second bioadhesive sealant component of the second container comprises an acrylate.

12. The bioadhesive sealant storage and preparation system of claim 1:
wherein the plurality of containers further comprises a third container having a third bioadhesive sealant component therein;
wherein the first container and the second container are positioned and configured within a receptacle of the adapter to maintain the first bioadhesive sealant component and the second bioadhesive sealant component separated for storage and to allow the mixing of the first bioadhesive sealant component and the second bioadhesive sealant component in response to an applied force.

13. The bioadhesive sealant storage and preparation system of claim 12, wherein the adapter further comprises a movable barrier positioned between the plurality of containers and the manifold, the movable barrier sized and configured to prevent fluid communication between the plurality of containers and the plurality of channels of the manifold when a force is applied and the movable barrier is positioned in a first position and to allow fluid communication between the plurality of containers and the plurality of channels of the manifold when the force is applied and the movable barrier is positioned in a second position.

14. The bioadhesive sealant storage and preparation system of claim 1, further comprising:
a syringe coupled to the outlet region of the adapter;
a pouch comprising a barrier separating a first region of the pouch from a second region of the pouch;
wherein the syringe is located in the first region of the pouch and the plurality of containers are located within the second region of the pouch;
wherein the first region of the pouch is sterile.

15. A tissue puncture closure system, comprising:
a syringe;
a bioadhesive sealant storage and preparation system, comprising:
a plurality of containers, the plurality of containers comprising:
a first container having a first bioadhesive sealant component therein;
a second container having a second bioadhesive sealant component therein;
a coupling device coupling the plurality of containers together, the coupling device comprising a protrusion;
an adapter movable relative to the coupling device, the adapter comprising:
a manifold comprising a plurality of channels formed therein;
an inlet region configured to connect to the plurality of containers and facilitate fluid communication between each container of the plurality of containers and a respective channel of the plurality of channels, the inlet region comprising a receptacle having a first recess and a second recess, the plurality of containers being movable between a first position at which the containers are connected to the receptacle with the protrusion of the coupling device in the first recess and a second position at which the containers are connected to the receptacle with the protrusion of the coupling device in the second recess, the plurality of containers being biased to the first position;
an outlet region configured to connect to the syringe and provide fluid communication between the syringe and the plurality of channels for delivery of bioadhesive sealant components to the syringe;
a delivery tube sized and configured for insertion into a tissue puncture, a proximal end of the delivery tube configured to connect to the syringe, a distal end of the delivery tube configured to deliver a bioadhesive sealant from the syringe to the tissue puncture.

16. The tissue puncture closure system of claim 15, further comprising:
a pouch comprising a barrier separating a first region of the pouch from a second region of the pouch;
wherein the syringe is located in the first region of the pouch and the plurality of containers are located within the second region of the pouch;
wherein the first region of the pouch is sterile.

\* \* \* \* \*